US007737700B2

(12) United States Patent
Kiesewetter et al.

(10) Patent No.: US 7,737,700 B2
(45) Date of Patent: Jun. 15, 2010

(54) ARRANGEMENT AND METHOD FOR DETECTING AIR INGREDIENTS

(75) Inventors: Olaf Kiesewetter, Geschwenda (DE); Anatolij Ewert, Ilmenau (DE); Volkmar Melchert, Martinroda (DE); Sven Kittelmann, Stadtilm (DE)

(73) Assignee: UST Umweltsensortechnik GmbH, Geschwenda (DE)

( * ) Notice: Subject to any disclaimer, the term of this patent is extended or adjusted under 35 U.S.C. 154(b) by 1203 days.

(21) Appl. No.: 11/286,209

(22) Filed: Nov. 23, 2005

(65) Prior Publication Data
US 2007/0116606 A1    May 24, 2007

(51) Int. Cl.
*G01N 27/00*    (2006.01)
(52) U.S. Cl. ............... 324/465; 73/31.02; 73/31.06; 73/335.02; 73/335.03; 73/335.04; 73/335.05; 422/90; 422/94; 422/95; 422/96; 422/97; 422/98; 340/632; 340/634; 324/464; 324/468; 435/807; 436/153
(58) Field of Classification Search ............... 73/31.01, 73/31.02, 23.34, 31.06, 335.02–335.05, 29.05; 422/82.01–82.04, 90, 94–98; 340/632, 634; 702/23, 24; 324/464, 465, 468; 435/807; 436/153
See application file for complete search history.

(56) References Cited
U.S. PATENT DOCUMENTS

| 4,390,869 | A | * | 6/1983 | Christen et al. ............ 340/632 |
| 4,443,793 | A | * | 4/1984 | Hall, Jr. ..................... 340/634 |
| 4,457,161 | A | * | 7/1984 | Iwanaga et al. ............ 73/31.05 |
| 4,464,244 | A | * | 8/1984 | Uchida et al. .............. 204/425 |
| 4,533,520 | A | * | 8/1985 | Bossart et al. ............... 422/96 |
| 4,586,143 | A | * | 4/1986 | Kaneyasu et al. ............ 702/27 |
| 4,638,443 | A | * | 1/1987 | Kaneyasu et al. ............ 702/24 |
| 5,627,305 | A | * | 5/1997 | Yun et al. .................... 73/23.2 |
| 5,635,628 | A | * | 6/1997 | Fleischer et al. ........... 73/31.06 |
| 5,824,271 | A | * | 10/1998 | Frank et al. ................... 422/98 |
| 6,046,054 | A |   | 4/2000 | McGeehin et al. |

(Continued)

FOREIGN PATENT DOCUMENTS

DE    38 33 295    4/1990

(Continued)

OTHER PUBLICATIONS

Harald Boettner, et al.; "Millenium Sensor System—MISSY"; Infoboerse Mikrosystemtechnik, Nr. 33, 2002.

*Primary Examiner*—Brian R Gordon
*Assistant Examiner*—Shogo Sasaki
(74) *Attorney, Agent, or Firm*—Jordan and Hamburg LLP

(57) ABSTRACT

Detecting air ingredients is obtained, a heater and gas sensitive acting layers are arranged on a substrate, which are connectable to an analyzing unit. Electrical resistances of n acting layers are connected in series; heater is a temperature sensor connected in parallel with this series connection, electrical resistance of heater is smaller than the sum of electrical resistances of acting layers and resistances are connected with a total of n+1 electrical terminals via electrodes so that heater is connected with two terminals and n−1 other terminals are connected with a respective junction that interconnects two acting layers. Heater is intermittently heated so that a predefined constant temperature of acting layers is achieved, temperature of acting layers is acquired by determining electrical resistance of heater; voltages in the series connection of acting layers are analyzed and a concentration of gases are determined from electrical resistances of acting layers.

15 Claims, 10 Drawing Sheets

U.S. PATENT DOCUMENTS 6,348,872 B1 * 2/2002 Otani et al. .................. 340/632
2005/0284208 A1 * 12/2005 Oishi et al. .................. 73/23.2

FOREIGN PATENT DOCUMENTS

| | | |
|---|---|---|
| DE | 197 42 696 | 5/1999 |
| EP | 0 354 486 | 2/1990 |
| EP | 0 833 147 | 4/1998 |
| EP | 0 945 722 | 9/1999 |
| FR | 2 797 498 | 2/2001 |
| GB | 2 376 565 | 12/2002 |

\* cited by examiner

ARRANGEMENT AND METHOD FOR DETECTING AIR INGREDIENTS

BACKGROUND OF THE INVENTION

The invention relates to an arrangement and to a method for detecting air ingredients, preferably for detecting air ingredients in buildings and vehicles.

For detecting air ingredients different embodiments are known, where metal-oxide gas sensors are used that are suitable for detecting airborne pollutants.

There are solutions that are suitable for particular lightly volatile substances (VOC) respectively, e.g. for car exhaust gases only. Up to now, there are no systems that are able to cover all of these ranges in order to control, for example, an air conditioning for rooms or to ventilate vehicle cabins in line with a pollution. As for many applications in vehicles the possible air flow rate is incessantly decreased, the known solutions fail these requirements.

For ventilating vehicles by a sensor controls there are known solutions from the late seventies that control the air condition by means of semiconductor gas sensors.

Because of severely changing ambient conditions as temperature, moisture or other influences, e.g. dust, relative levels are used for open or closed loop control. It would be desirable to have so-called artificial noses by which car exhausts as well as different smells can be detected such that the sensor can be used both indoors and outdoors and a sensor-internal monitoring of acting layers take place.

New developments in the area of semiconductor gas sensors, e.g. array structures, multichips and the like, enable to construct artificial noses that make it possible to much better cover the chemical space of attributes and to better copycat the properties of odor-guided sense organs by means of neuronal networks. Using this system it is possible to detect smallest concentrations in the ppb magnitude (e.g. inside a vehicle) as well as high concentrations in the ppm magnitude (e.g. outdoors). Besides, the drift is smaller than for single sensors, because no superimposed signals result from present gases. A disadvantage of this otherwise very advantageous design is its price, because several sensors and a multitude of electrical contacting wires are needed.

BRIEF SUMMARY OF THE INVENTION

The subject of the invention is to specify an arrangement and a method of the type initially mentioned, where an analysis is possible cost-efficiently using several sensitive layers.

The arrangement according to the invention is a single sensor element having preferably three acting layers sensitive to certain gases, which generate analyzable signals, wherein a chemical space of attributes can be acquired in a complex way.

The arrangement stands out by a series of advantages. These are amongst others:
  Different air ingredients can be detected;
  the measurement is performed using preferably three different acting layers, wherein only a total of four terminals is needed for connecting the acting layers and a heater with an analyzing unit;
  the arrangement allows to acquire drift and contamination effects of the acting layers;
  the arrangement can be produced very cost-efficiently and can be placed, for example, in a standard housing;
  the acting layers can be arranged vertically or horizontally.
In the following, the invention is further illustrated with embodiments for controlling a ventilation of motor vehicle cabins in line with a pollution. The examples described are suitable for applications in other closed rooms, too.

BRIEF DESCRIPTION OF THE DRAWINGS

Accompanying the specification are figures which assist in illustrating the embodiments of the invention, in which.

DETAILED DESCRIPTION OF THE INVENTION

The arrangement is placed on a substrate 1 in a standard housing. The analysis of the signals is performed by means of an analyzing unit using a predefined analyzing algorithm or using neuronal networks.

Figure 1:
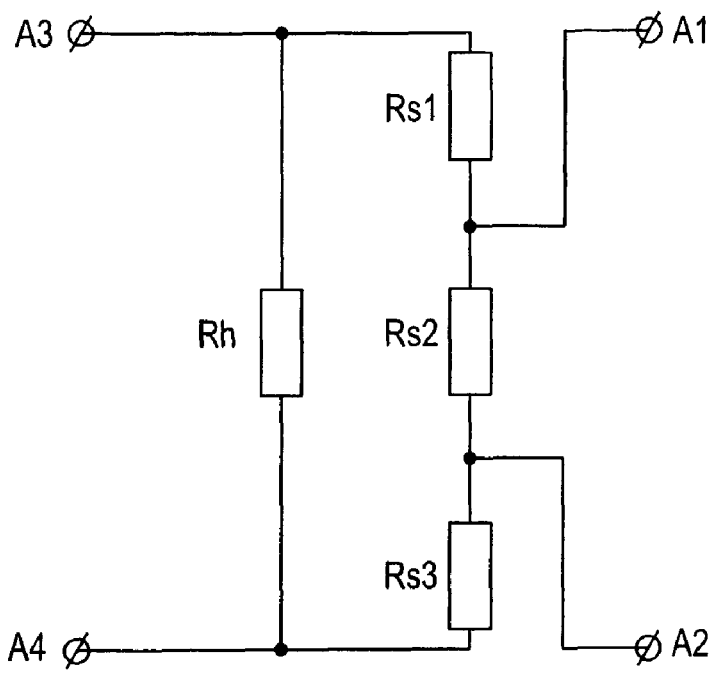
FIG. 1 the electrical circuit of the sensor arrangement.

FIG. 1 illustrates the electrical circuit of the sensor arrangement. The three resistances Rs1, Rs2 and Rs3 of the acting layers S are connected in series. The acting layers include either or both of $SnO_2$ or $WO_3$. The resistance Rh for heating and temperature measurement is connected in parallel with the series connection of the acting layers S. A platinum resistor having an electrical resistance value of 5 to 150 Ohm, preferably of 10 to 30 Ohm, at 0° C. is used as the resistance Rh. This value is significantly smaller than the sum of the resistances Rs1, Rs2, Rs3 of the acting layers S, which respectively have values of 1 to 10 MOhm, preferably of 10 to 100 kOhm. The heating resistance Rh is connected to the electrical terminals A3 and A4. The terminals A1 and A2 are connected to the electrical junctions of the resistances Rs1-Rs2 and Rs2-Rs3.

Figure 2:
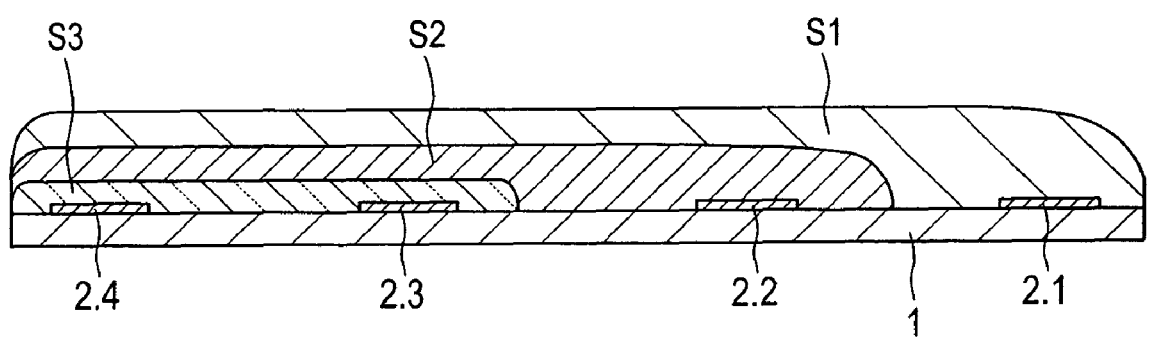
FIG. 2 an embodiment having three acting layers arranged above each other.

FIG. 2 shows an embodiment where four electrodes 2.1 ... 2.4 and three sensitive acting layers S1, S2 and S3 are arranged above each other on one substrate 1, wherein each electrode connects two acting layers, respectively.

Figure 3:
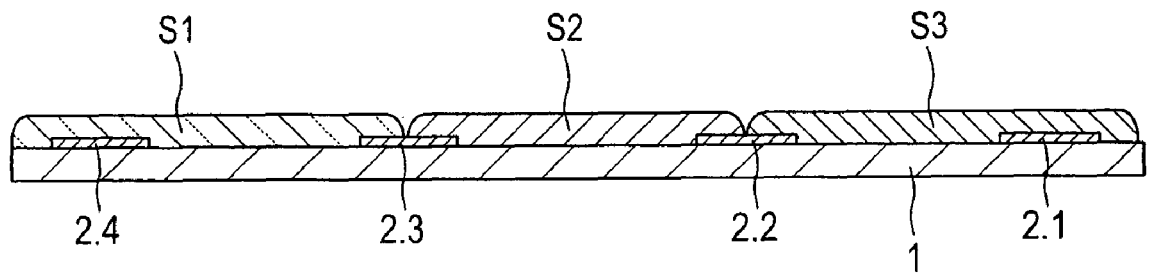
FIG. 3 an embodiment having three acting layers arranged side by side.

In case of the sensor arrangement depicted in FIG. 3 the three sensitive acting layers S1, S2 and S3 are arranged side by side.

Figure 4:
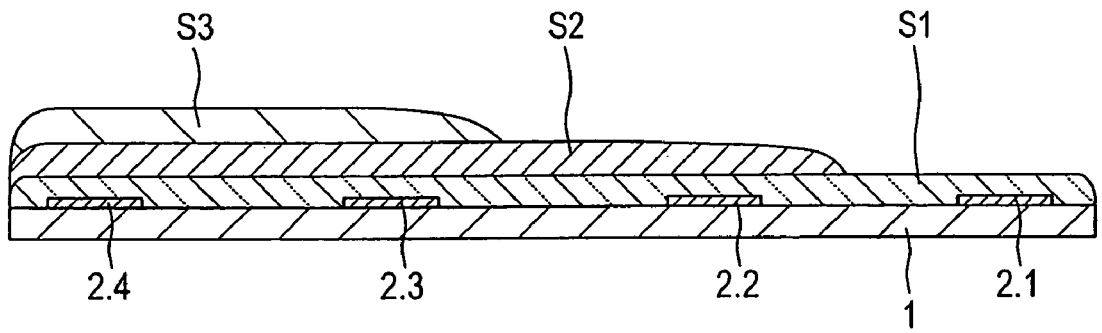
FIG. 4 an embodiment having three acting layers offset above each other.

In FIG. 4 an embodiment is shown having the three acting layers S1, S2 and S3 offset above each other. It is also possible that the gas-sensitive element consists from one layer comprising different acting sections.

Figure 5:
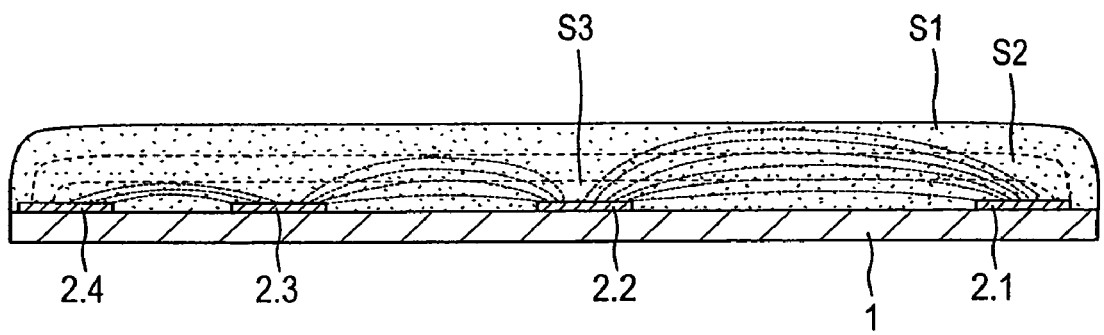
FIGS. 5 and 6 an embodiment having arranged the electrodes in varying distances and having integrated the sensitive elements into a layer consisting of differently doped acting layers.
Figure 6:
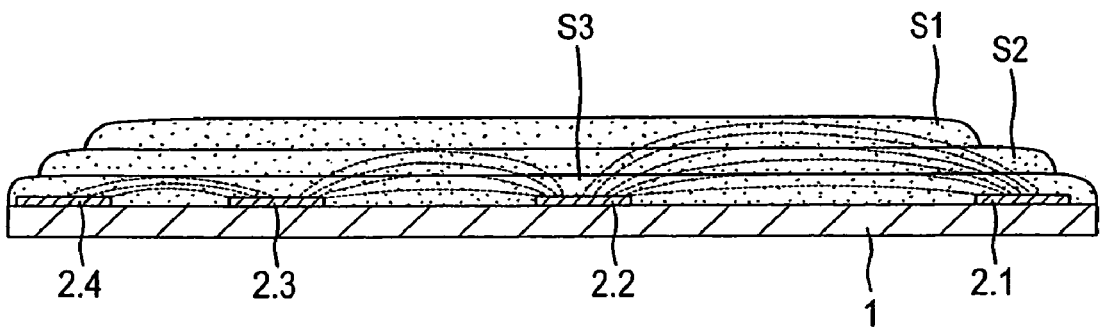

In case of the alternatives depicted in FIGS. 5 and 6 the electrodes 2.1 ... 2.4 are arranged on the substrate 1 in varying distances from each other. Therefore, the current between adjacent electrodes 2 will penetrate the acting layers to different depths and will thus run through different acting layers or different acting layer sections such that external influencing variables that cause changes of properties of the acting layers will have different effects between different pairs of electrodes. Such changes are caused, for example, by contaminations. This leads to relative changes in the resistances, the acquisition of which enables a statement about the change (contamination) in the acting layers. In the arrangement of FIG. 6 the acting layers are arranged above each other in the shape of stair-steps such that this effect is even stronger. The gas to be detected diffuses through the porous acting layers and causes different reactions in different layer sections. Depending on the arrangement of the layer sections and of the electrodes, selective signals can be created. Hence, it is possible to tune in the arrangement to a certain gas of interest.

Figure 7:
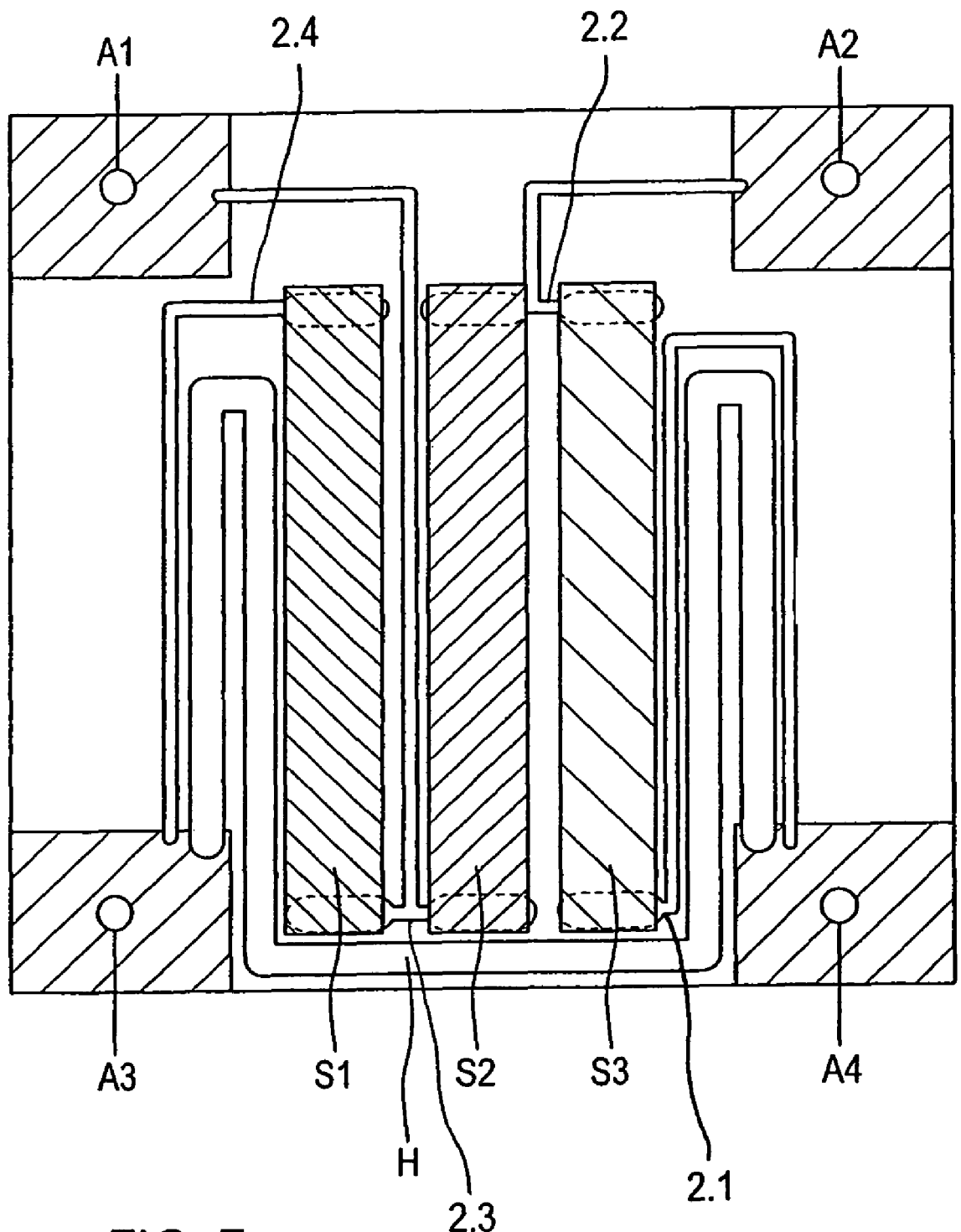
FIG. 7 the top view of an arrangement arranged onto a chip.

The top view on a chip carrying the sensor arrangement is shown in FIG. 7. The chip illustrated in this example is designed quadratically and provided with contact pads for the electrical terminals A1 ... A4 at its corners, the terminals A1 ... A4 being connected with the electrodes 2.1 ... 2.4. The electrodes 2.2 and 2.3 connect the terminals A1 and A2 with the junctions of the acting layers S1-S2 and S2-S3, respectively, while the terminals A3 and A4 are connected with the ends of the heater H and the electrodes 2.1 and 2.4, respectively, the electrodes 2.1 and 2.4 leading to the ends of the acting layers S1 and S3, respectively: The heater H is a heater resistor disposed on the surface of the substrate laterally adjacent at least one of the acting sensing layers S1-S3 and has a heater resistance, and the lateral direction extends parallel the surface of the substrate.

Figure 8:
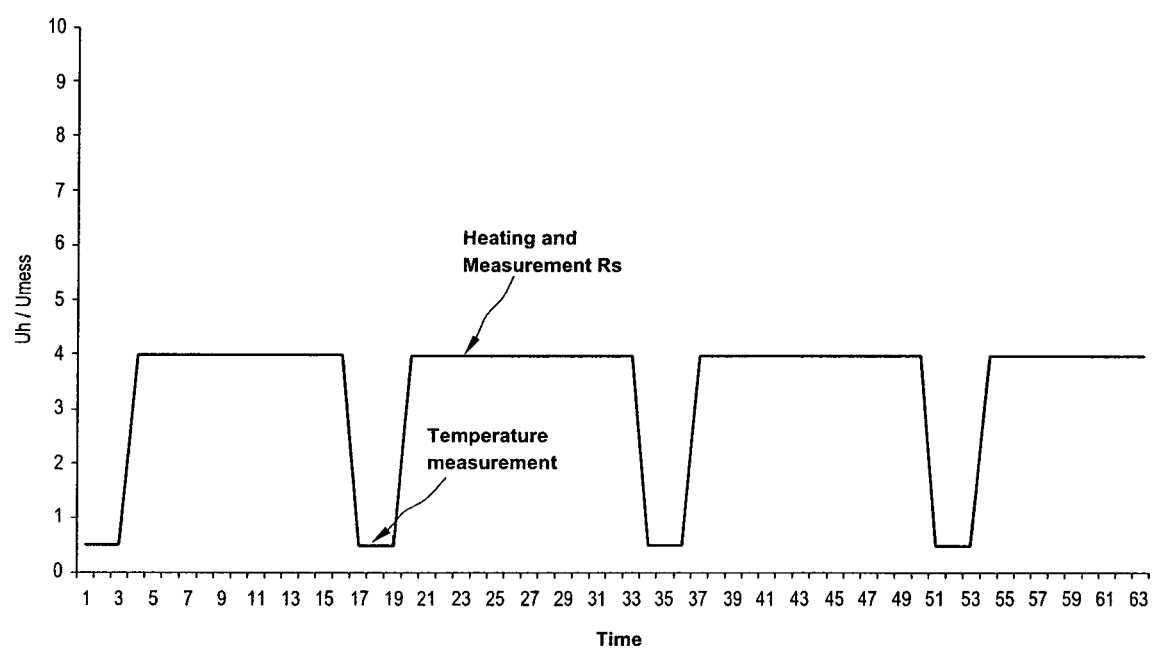
FIGS. 8 to 10 the chronological courses of different operation modes of the arrangement.
Figure 9:
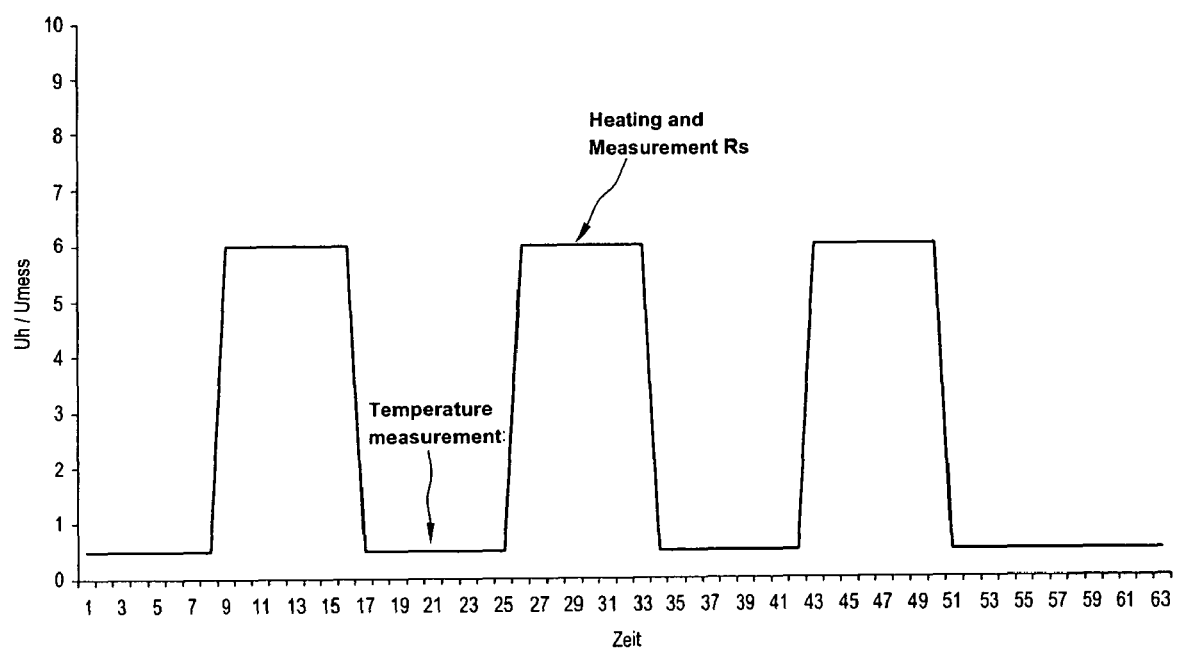
Figure 10:
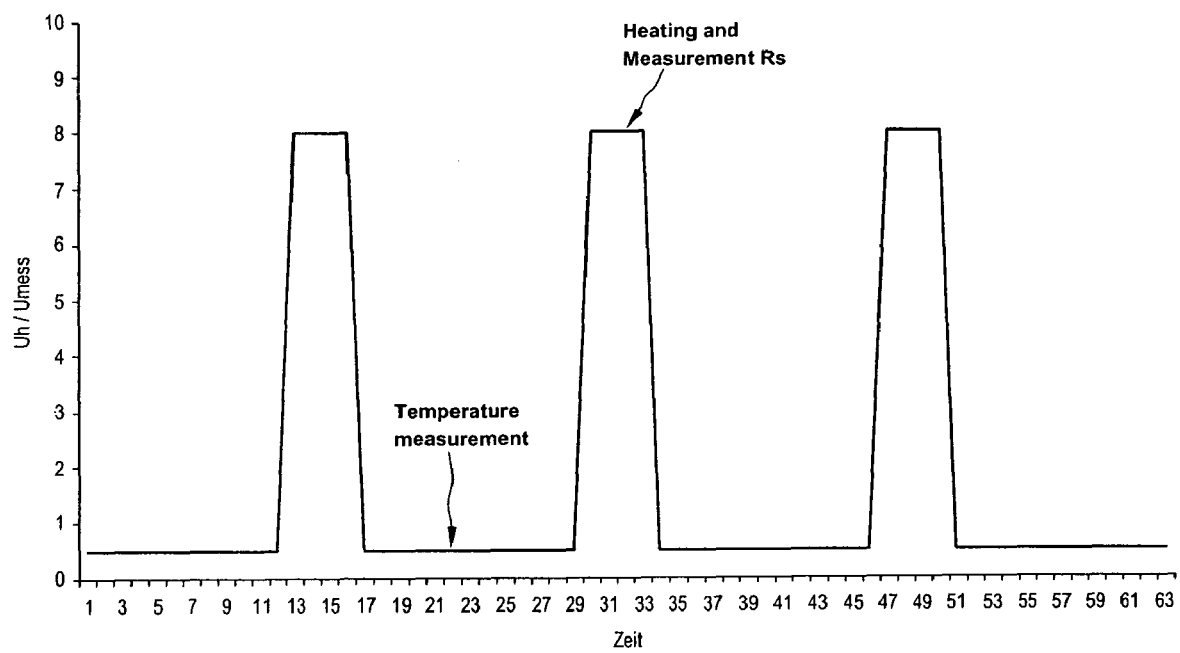

In FIGS. 8 to 10 variants for the chronological course of the voltages available at the terminals A3 and A4 of the heater H are reproduced. The arrangement is respectively heated to a predefined temperature, wherein the heating resistance Rh and thus the temperature of the arrangement can be determined from a current-voltage measurement. The temperature can be adjusted by selecting the voltage and the pulse ratio.

In doing so, the acting layers are heated such that the voltages resulting across the acting layers S1, S2 and S3 can be acquired at defined temperatures. These voltages represent a function of the gas concentration. The voltage potentials at the electrical junctions located between the acting layers S1 and S2 as well as between S2 and S3 can be picked off at the terminals A1 and A2 that are conductively connected to these junctions.

Figure 11:
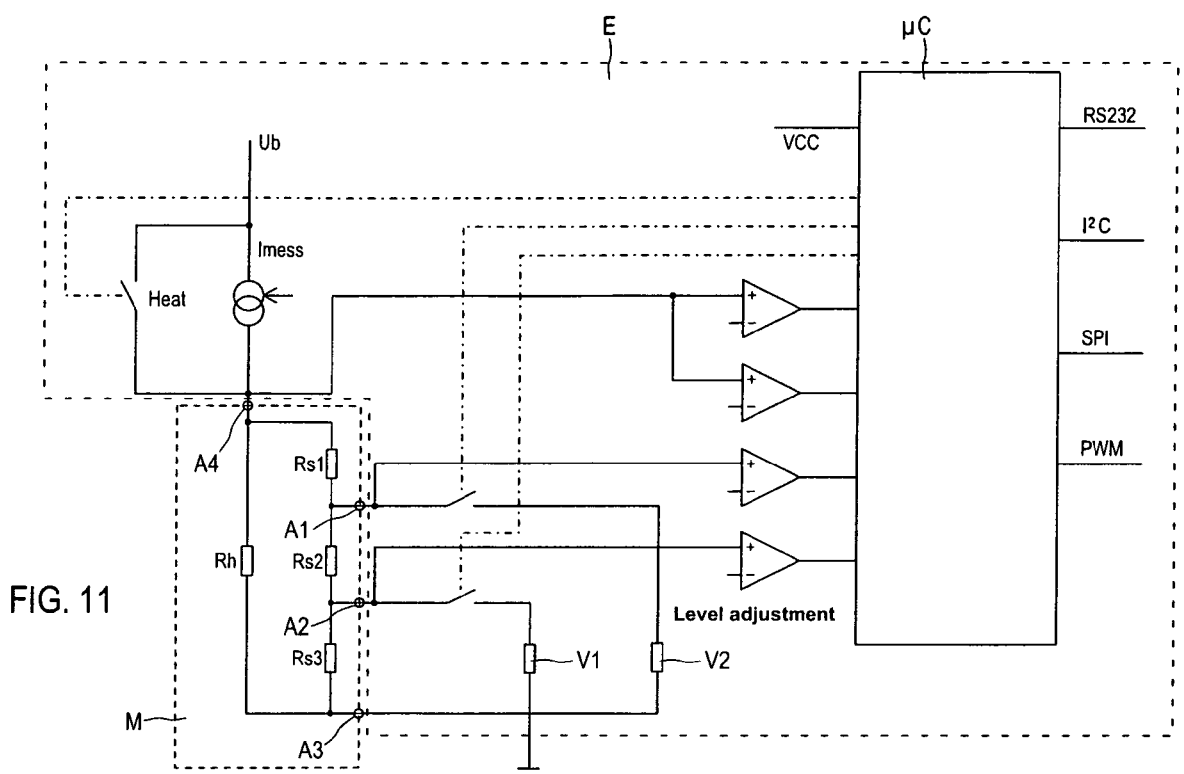
FIG. 11 the circuit diagram for an arrangement with an analyzing unit.

FIG. 11 illustrates the circuit diagram for an arrangement where the measuring arrangement M is connected to an analyzing unit E. The measuring arrangement M consists of a parallel connection of resistances where the resistance Rh for heating and temperature measurement is connected in parallel with the electrical resistances Rs1, Rs2 and Rs3 of the acting layers S. Besides, the heating and temperature measurement resistance Rh is connected to the voltage source via the terminal A4. The heating current flowing through the heating and temperature measurement resistance Rh can be turned on and off in the way described above by means of a switch controlled by a microcontroller μC. The terminals A1, A2 and A3 connect the analyzing unit E with the electrical resistances Rs1, Rs2 and Rs3 of the acting layers S. The analyzing unit E comprises the comparison resistances V1 and V2, wherein V1 can be switched in parallel with the acting layer resistance Rs3 and V2 can be switched in parallel with the series connection of Rs2 and Rs3. The switching-on of the comparison resistances V1 and V2 is controlled by the microcontroller μC such that the raw signals directly obtained from the voltages across the acting layer resistances Rs1, Rs2 and Rs3 as well as signals that are obtained from a parallel connection of the comparison resistances V1 and V2 with the electrical resistances Rs2 and Rs3 of the acting layers S are available for the analysis. As the values of the comparison resistances V1 and V2 are known, a statement about the absolute value of the resistance values Rs1, Rs2 and Rs3 of the acting layers S can be made therefrom by which a statement about the existence and/or the concentration of a certain gas can be given.

Figure 12:
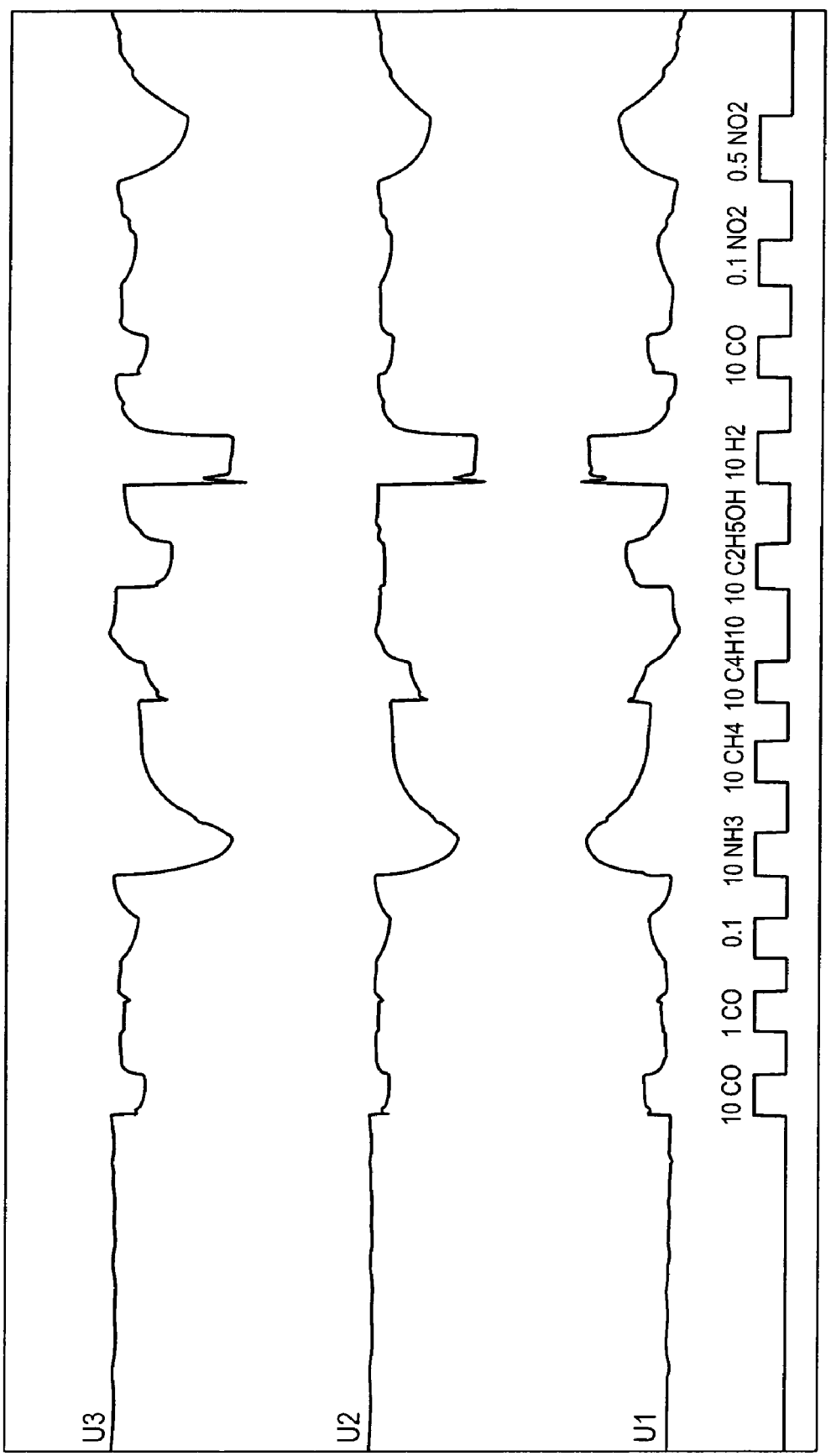
FIGS. 12 and 13 courses of measurement values obtained from different gas samples.
Figure 13:
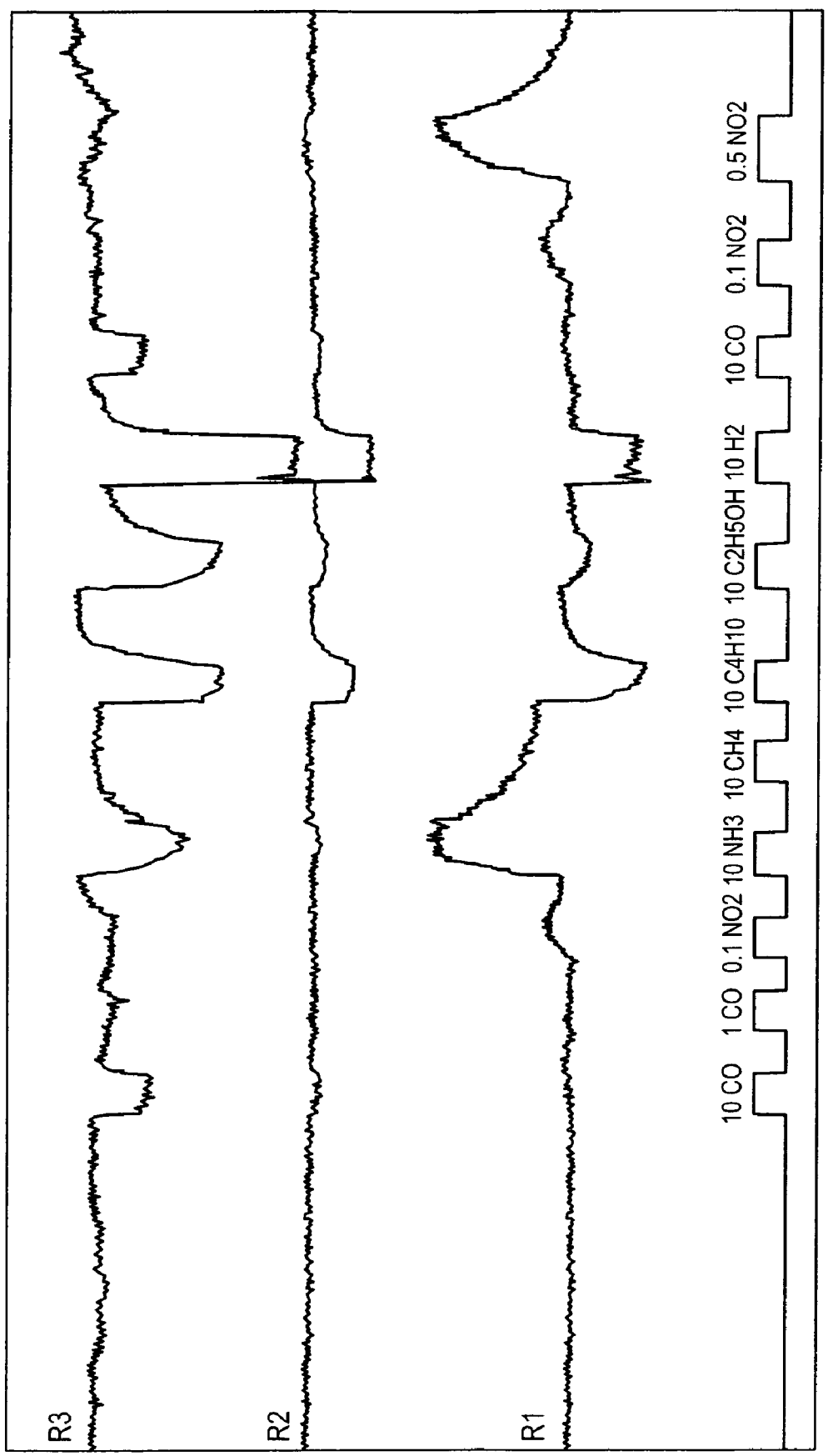

The FIGS. 12 and 13 show courses of measurement values that have been obtained using the arrangement according to the invention in detecting different gas samples that have been fed to it consecutively.

In FIG. 12, the chronological course of the signals for the raw values U1, U2 and U3 picked off at the terminals A1, A2 and A3 are depicted. FIG. 13 shows the course of the real values R1, R2 and R3 determined by the analyzing unit E considering the comparison resistances V1 and V2. It can be seen in the diagrams that a statement about the existence of a gas mixture is possible without considering the absolute values determined using the comparison resistances V1 and V2 indeed. However, by analyzing the absolute values a unique statement about the existence and, if necessary, the concentration of a certain single gas is possible in addition.

Figure 14:
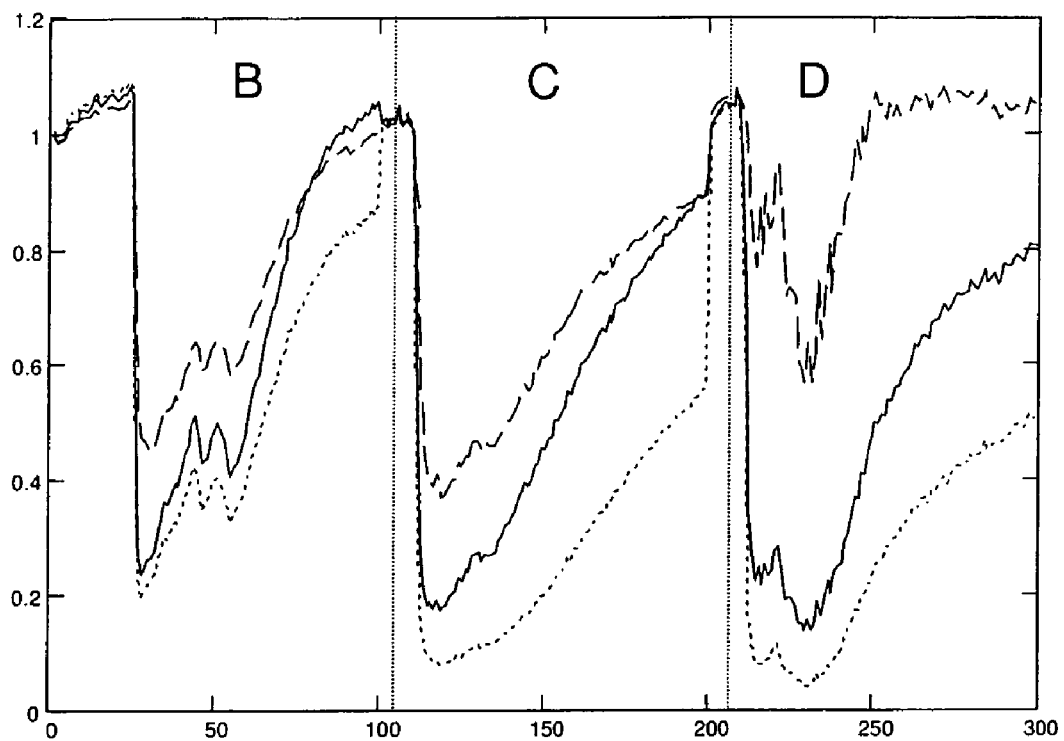
FIG. 14 normalized courses of measurement values of three different gas samples.

FIG. 14 shows the reaction of three acting layers S1, S2, S3 of a sensor arrangement according to FIG. 7 to successively and alternatively supplying three different gases B, C, D in approximately equal, respectively increasing concentrations. In the graph the signals corresponding to the raw values U1, U2, U3 are normalized. A signal value of one accordingly means no gas detected or clean air, respectively. A smaller value corresponds to a smaller voltage across the respective acting layer S1, S2 or S3 and thus a higher concentration of a detected gas B or C or D. It can be seen that the three acting layers S1, S2, S3 of the chip react to the different gases B, C, D to different degrees. This can be used for distinguishing different gases or gas mixtures. However, with a single measuring data set comprising the raw values U1, U2, U2 or, preferably, the real values R1, R2, R3 an analysis concerning type and concentration of a gas sample is possible with large effort at best, if at all. An arrangement of n sensors yields a point in an n-dimensional sample space for each concentration. Besides, gas mixtures can occur that do not create a simple linear superimposition of the several signals because of cross sensitivities.

Hence, according to the invention a transformation rule can be determined from a set of calibration data sets using a principal component analysis, the transformation rule assigning a set of principal components to a measuring data set, which have a higher significance because of the reduced number of variables that have to be considered. In particular for a larger number of acting layers a compact statement about the type and the amount of the detected gas or gases B, C, D can be determined from a measuring data set. The principal component analysis (PCA) is among the multivariate methods of statistics. A plurality of variables, e.g. the signals of several gas sensors, are regarded together in order to reproduce their dependency structure. The principal component analysis makes it possible to extract few relevant factors from data having many properties resulting in a small loss of information by using a principal axis transformation.

The application of the principal component analysis for analyzing signals requires a calibration measurement adjusted to the utilized acting layers S1, S2, S3 and to the expected gases. In such a calibration all expected scenarios should be covered by measurements. With the obtained data the transformation rule is determined that can be used for analyzing the signals. By the transformation the discrimination between single events, in the present case certain concentrations of different gases B, C, D, is eased, because their distance in the lower-dimensional, for example, two- or three-dimensional sample space is maximized. Thereby it is simpler or possible in the first place to establish certain conditions for identifying these gases B, C, D and to transfer them to the signal analysis. The conditions can comprise, for example, a respective threshold value for each principal component, which is tested for an exceedance.

For example, in the present embodiment a two-dimensional reproduction of the respective measuring data set is created using the transformation rule determined in the principal component analysis, the reproduction containing nearly all information about the signals of the chip's three acting layers S1, S2, S3. The two-dimensional reproduction consists of the principal components X and Y.

Figure 15:
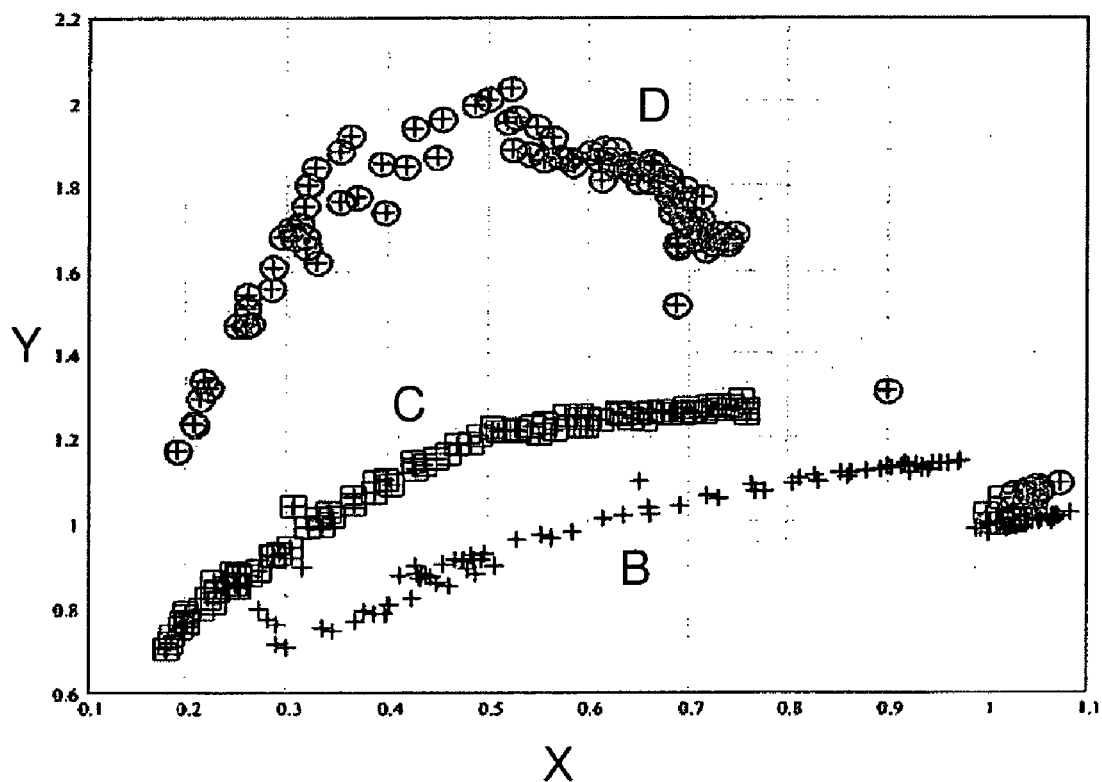
FIG. 15 principal components of the normalized measurement values.

In FIG. 15, the resulting principal components X and Y of such principal component transformations of the courses of the measurement value of FIG. 14 are depicted. In this diagram, the reference point ($X=1, Y=1$) corresponds to a situation of clean air, in which a corresponding signal is present from the three acting layers S1, S2, S3. For increasing concentration of a gas B or C or D the respective measuring point $(X,Y)$ moves away from this reference point $(1,1)$. Therein, the distance is a degree for the concentration of the measured gas B, C, D while the direction of the deviation from the reference point $(1,1)$ describes the type of the gas B, C, D. Therewith, it is possible to perform a qualitative as well as a quantitative measurement of different gases and gas mixtures concerning type and amount of the respective gas or gas mixture using the sensor arrangement.

In other embodiments of the invention an arbitrary number of principal components can be acquired by means of the principal components analysis. Die number of two principal components X, Y used in the examples above is merely selected for a simple understanding.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. A sensor device for sensing at least one gas in a gaseous atmosphere, comprising:
    a substrate having first and second surfaces opposing one another;
    first through nth sensing layers disposed on said substrate and connected to each other in series, said first through nth sensing layers respectively having a first through nth sensing layer electrical resistance, and said first trough nth sensing layers being configured to present differing compositions thereof to said gaseous atmosphere, each of said differing compositions being such as to change a respective one of said first through nth sensing layer electrical resistances in presence of a respective gas;
    said first through tab sensing layers being disposed electrically connected together in a series connection with each other from said first sensing layer to said nth sensing layer absent intervening resistors;
    first through (n+1)th electrical terminals disposed on said first surface of said substrate and configured for accepting electrical connections thereto from external to said substrate;
    first through (n+1)th electrode conductors disposed on said substrate and respectively contacting said first through (n+1)th electrical terminal, said first through (n+1) th electrode conductors being disposed such that, wherein x varies from one to n, said first and said x th electrode conductors are disposed to conduct current passing through said first through said x th sensing layer;
    a heater resistor disposed on said first surface of said substrate laterally adjacent at least one of said first through nth sensing layers and having a heater resistance, wherein a lateral direction extend parallel the first surface of the substrate;
    n being at least three, wherein:
        said heater resistor has first and second heater terminals that arranged in a parallel connection to the series connection of said first through nth sensing layers, said parallel connection being effected by:
            said first electrical terminal and said first electrode conductor directly connecting to said first sensing layer and said first heater terminal; and
            said (n+1) th electrical terminal and said (n+1) th electrode conductor connecting to said nth sensing layer and said second heater terminal; and
        said heater resistance is less than a sum of said first through nth sensing layer electrical resistances.

2. The sensor device of claim 1, wherein said first through nth sensing layers are each disposed in contact with the first surface of the substrate and are arranged laterally adjacent each other.

3. The sensor device of claim 2, wherein m is an integer ranging from 2 to n, and said m th electrode conductor is in direct contact with both said (m−1)th sensing layer and said m th sensing layer to thereby effect the series connection between said (m−1)th sensing layer and said m th sensing layer.

4. The sensor device of claim 3, further comprising:
    an analyzing unit including a controller;
    said analyzing unit having electrical connections to said substrate for effecting measurements using said first through n th sensing layers by intermittently driving said heater resistor via said first and said (n+1) electrical terminals and sensing potentials via at least said second through nth electrical terminals, said electrical connections for effecting measurements using said first through n th sensing layers being limited so as to consist of connections via said first through (n+1) th electrical terminals;
    said analyzing unit being configured to selectively apply a heater driving potential to said heater resistor via said electrical connections under control of said controller;
    said analyzing unit being configured to sense potentials at least via said second trough nth electrical terminals under control of said controller;
    said analyzing unit being configured to apply at least one comparison resistance in parallel with at least one of said first trough nth sensing layers so that signals detected from a potential across the at least one comparison resistance are compared with a potential across said at least one of said first through nth sensing layers without said at least one comparison resistance applied, wherein the analyzer further includes being configured to sense a potential of said (n+1)th electrical terminal under control of said controller, and the controller of the analyzer unit is configured to:
        intermittently drive the heater so that a predefined constant temperature of the first through nth sensing layers achieved;

acquire a temperature of the first through nth sensing layers by determining the heater resistance of the heater;

analyze the potentials sensed at the second through (n+1)th electrical terminals so as to determine the first through nth sensing layer electrical resistances; and determine an existence and/or a concentration of predetermined gases based on the first through nth sensing layer electrical resistances.

5. The sensor device of claim 2, wherein:

m is an integer ranging from 2 to (n+1);

said m th electrode conductor is in direct contact with said (m−1)th sensing layer and not in direct contact with said m th sensing layer but is disposed proximate a junction of said (m−1)th sensing layer and said m th sensing layer whereat said junction contacts said substrate of said substrate;

the series connection of said first through nth sensing layers disposed on said substrate is effected by said first through nth sensing layers contacting each other by overlying each other at least in a direction normal to the first surface of the substrate; and said m th sensing layer extends further over said first surface of said substrate than said (m−1)th sensing layer so as to contact said first surface of said substrate at an area adjacent an area whereat said (m−1)th sensing layer contacts said substrate.

6. The sensor device of claim 5, further comprising:

an analyzing unit including a controller;

said analyzing unit having electrical connections to said substrate for effecting measurements using said first through n th sensing layers by intermittently driving said heater resistor via said first and said (n+1) electrical terminals and sensing potentials via at least said second through nth electrical terminals, said electrical connections for effecting measurements using said first through n th sensing layers being limited so as to consist of connections via said first through (n+1) th electrical terminals;

said analyzing unit being configured to selectively apply a heater driving potential to said heater resistor via said electrical connections under control of said controller;

said analyzing unit being configured to sense potentials at least via said second through nth electrical terminals under control of said controller;

said analyzing unit being configured to apply at least one comparison resistance in parallel with at least one of said first through nth sensing layers so that signals detected from a potential across the at least one comparison resistance are compared with a potential across said at least one of said first through nth sensing layers without said at least one comparison resistance applied, wherein the analyzer further includes being configured to sense a potential of said (n+1)th electrical terminal under control of said controller, and the controller of the analyzer unit is configured to:

intermittently drive the heater so that a predefined constant temperature of the first through nth sensing layers is achieved;

acquire a temperature of the first through nth sensing layers by determining the heater resistance of the heater;

analyze the potentials sensed at the second through (n+1)th electrical terminals so as to determine the first through nth sensing layer electrical resistances; and determine an existence and/or a concentration of predetermined gases based on the first through nth sensing layer electrical resistances.

7. The sensing device of claim 1, wherein:

said first through nth sensing layers are disposed in the series connection by sequentially lying atop one another wherein, said first sensing layer is disposed in contact with the first surface of the substrate and in direct contact with each of said first through (n+1)th electrode conductors, and said m th sensing layer is disposed over and on contact with said (m−1)th sensing layer, wherein m is an integer varying from 2 to n; and wherein p is an integer varying from 2 to (n+1), said first through (n+1) th electrode conductors are disposed on said substrate such that said p th electrode conductor is disposed so as to sense a potential substantially determined by current traveling through said first through (p−1) th sensing layers.

8. The sensing device of claim 7, wherein:

said first through (n+1) th electrode conductors are disposed under said first sensing layer spaced apart at substantially constant intervals; and wherein y is an integer varying from 2 to (n+1), said y th sensing layer has an area boundary offset inwardly from an area boundary of said (y−1)th sensing layer such that said y th electrode conductor is disposed so as to sense a potential substantially determined by current traveling through said first through (y−1)th sensing layers.

9. The sensor device of claim 8, further comprising:

an analyzing unit including a controller;

said analyzing unit having electrical connections to said substrate for effecting measurements using said first through n th sensing layers by intermittently driving said heater resistor via said first and said (n+1) electrical terminals and sensing potentials via at least said second through nth electrical terminals, said electrical connections for effecting measurements using said first through n th sensing layers being limited so as to consist of connections via said first through (n+1)th electrical terminals;

said analyzing unit being configured to selectively apply a heater driving potential to said heater resistor via said electrical connections under control of said controller;

said analyzing unit being configured to sense potentials at least via said second through nth electrical terminals under control of said controller;

said analyzing unit being configured to apply at least one comparison resistance in parallel with at least one of said first through nth sensing layers so that signals detected from a potential across the at least one comparison resistance are compared with a potential across said at least one of said first through nth sensing layers without said at least one comparison resistance applied, wherein the analyzer further includes being configured to sense a potential of said (n+1)th electrical terminal under control of said controller, and the controller of the analyzer unit is configured to:

intermittently drive the heater so that a predefined constant temperature of the first through nth sensing layers is achieved;

acquire a temperature of the first through nth sensing layers by determining the heater resistance of the heater;

analyze the potentials sensed at the second through (n+1)th electrical terminals so as to determine the first through nth sensing layer electrical resistances; and determine an existence and/or a concentration of predetermined gases based on the first through nth sensing layer electrical resistances.

10. The sensing device of claim 7, wherein:

said first through (n+1)th electrode conductors are disposed under and in direct contact with said first sensing layer; and said first through (n+1) th electrode conductors are disposed spaced by first through n th intervals such that, wherein y is an integer varying from 1 to n:

said y th electrode conductor is spaced from said (y+1)th electrode conductor by said y th interval from said p th electrode conductor; and said first through (n+1)th electrode conductors are successively spaced apart from each other by said first through n th intervals of successively increasing distance such that said (y+1)th electrode conductor is disposed so as to sense a potential substantially determined by current traveling through said first through y th sensing layers.

11. The sensor device of claim 10, further comprising:

an analyzing unit including a controller;

said analyzing unit having electrical connections to said substrate for effecting measurements using said first through n th sensing layers by intermittently driving said heater resistor via said first and said (n+1)electrical terminals and sensing potentials via at least said second through nth electrical terminals, said electrical connections for effecting measurements using said first through n th sensing layers being limited so as to consist of connections via said first through (n+1)th electrical terminals;

said analyzing unit being configured to selectively apply a heater driving potential to said heater resistor via said electrical connections under control of said controller;

said analyzing unit being configured to sense potentials at least via said second trough nth electrical terminals under control of said controller;

said analyzing unit being configured to apply at least one comparison resistance in parallel with at least one of said first through nth sensing layers so that signals detected from a potential across the at least one comparison resistance are compared with a potential across said at least one of said first through nth sensing layers without said at least one comparison resistance applied, wherein the analyzer further includes being configured to sense a potential of said (n+1)th electrical terminal under control of said controller, and the controller of the analyzer unit is configured to:

intermittently drive the heater so that a predefined constant temperature of the first through nth sensing layers is achieved;

acquire a temperature of the first through nth sensing layers by determining the heater resistance of the heater;

analyze the potentials sensed at the second through (n+1)th electrical terminals so as to determine the first through nth sensing layer electrical resistances; and determine an existence and/or a concentration of predetermined gases based on the first through nth sensing layer electrical resistances.

12. A method of determining presence of a predetermined gas in a gaseous atmosphere using the sensor device of claim 11, comprising:

exposing the substrate of the sensor device to said gaseous atmosphere; and extracting the determination made by the controller of the analyzer unit as an indication of existence of the predetermined gas in the gaseous atmosphere.

13. A method of determining presence of a predetermined gas in a gaseous atmosphere using the sensor device of claim 9, comprising:

exposing the substrate of the sensor device to said gaseous atmosphere; and reading the determination made by the controller of the analyzer unit as an indication of existence of the predetermined gas in the gaseous atmosphere.

14. A method of determining presence of a predetermined gas in a gaseous atmosphere using the sensor device of claim 6, comprising:

exposing the substrate of the sensor device to said gaseous atmosphere; and reading the determination made by the controller of the analyzer unit as an indication of existence of the predetermined gas in the gaseous atmosphere.

15. A method of determining presence of a predetermined gas in a gaseous atmosphere using the sensor device of claim 4, comprising:

exposing the substrate of the sensor device to said gaseous atmosphere; and reading the determination made by the controller of the analyzer unit as an indication of existence of the predetermined gas in the gaseous atmosphere.

* * * * *